[`US010094845B2`]

(12) United States Patent
Itoh (10) Patent No.: US 10,094,845 B2
(45) Date of Patent: Oct. 9, 2018

(54) SAMPLE PROCESSING APPARATUS AND SAMPLE PROCESSING METHOD

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 0 days.

(21) Appl. No.: 14/944,628

(22) Filed: Nov. 18, 2015

(65) Prior Publication Data

US 2016/0137426 A1 May 19, 2016

(30) Foreign Application Priority Data

Nov. 18, 2014 (JP) ................................. 2014-233954

(51) Int. Cl.
*B65G 47/74* (2006.01)
*B01L 3/14* (2006.01)
*G01N 35/04* (2006.01)

(52) U.S. Cl.
CPC ..... *G01N 35/04* (2013.01); *G01N 2035/0406* (2013.01); *G01N 2035/0465* (2013.01); *G01N 2035/0498* (2013.01)

(58) Field of Classification Search
CPC ... G01N 2035/0406; G01N 2035/0465; B65G 47/22; B65G 47/244; B65G 47/24
See application file for complete search history.

(56) References Cited

U.S. PATENT DOCUMENTS

| 4,982,553 | A | * | 1/1991 | Itoh | B67B 7/02 |
| | | | | | 198/346.2 |
| 5,050,723 | A | * | 9/1991 | Herzog | B65G 47/248 |
| | | | | | 198/395 |
| 2004/0005245 | A1 | * | 1/2004 | Watson | B65G 47/1471 |
| | | | | | 422/65 |
| 2004/0109791 | A1 | * | 6/2004 | Itoh | B65G 47/1478 |
| | | | | | 422/63 |
| 2005/0265896 | A1 | * | 12/2005 | Itoh | G01N 35/04 |
| | | | | | 422/65 |
| 2007/0048185 | A1 | * | 3/2007 | Dupoteau | B01F 11/0002 |
| | | | | | 422/68.1 |

(Continued)

FOREIGN PATENT DOCUMENTS

| CN | 1860359 | 11/2006 |
| DE | 2 316 355 | 10/1974 |

(Continued)

OTHER PUBLICATIONS

Introduction to Stepper Motors, http://mechatronics.mech.northwestern.edu/design_ref/actuators/stepper_intro.html, accessed Dec. 1, 2016, pp. 1-3, date unknown.*

(Continued)

*Primary Examiner* — Kathryn Wright
(74) *Attorney, Agent, or Firm* — Nixon & Vanderhye P.C.

(57) ABSTRACT

According to an embodiment, a sample processing apparatus includes a detection section configured to detect pose information regarding a sample container which is configured to house a sample; and a raising section which turns the sample container in a predetermined direction based on the pose information regarding the sample container to raise the sample container.

6 Claims, 7 Drawing Sheets

(56) References Cited

U.S. PATENT DOCUMENTS

| | | | |
|---|---|---|---|
| 2010/0111767 A1 | 5/2010 | Yonekura et al. | |
| 2010/0233754 A1* | 9/2010 | Guex | G01N 35/02 435/29 |
| 2013/0278927 A1* | 10/2013 | Johnson | G01N 21/9054 356/240.1 |
| 2014/0363259 A1* | 12/2014 | Lorenzen | G01N 35/04 414/224.01 |

FOREIGN PATENT DOCUMENTS

| | | |
|---|---|---|
| EP | 0 819 470 | 1/1998 |
| JP | 2005-300357 | 10/2005 |
| JP | 2008-268033 | 11/2008 |
| JP | 2010-107400 | 5/2010 |
| JP | 2011-16659 | 1/2011 |
| KR | 10-2007-0026299 | 3/2007 |
| WO | WO 99/28724 | 6/1999 |

OTHER PUBLICATIONS

Extended European Search Resort issued in Application No. 15194516.9 dated Apr. 13, 2016.
Taiwanese Office Action issued in App. No. 104137742 dated Aug. 5, 2016 (w/ translation.
Chinese Office Action issued in App. No. 201511028221.0 dated Feb. 17, 2017 (w/ translation.
Taiwanese Office Action issued in App. No. 104137742 dated Feb. 21, 2017 (w/ translation).
Korean Office Action issued in Appln. No. 10-2015-0161176 dated Mar. 29, 2017 (w/ translation).
Korean Office Action issued in Appln. No. 10-2015-0161176 dated Sep. 26, 2017 (with translation).
Office Action issued JP Appln. No. 2014-233954 dated Jun. 5, 2018 (w/ translation).

* cited by examiner

SAMPLE PROCESSING APPARATUS AND SAMPLE PROCESSING METHOD

CROSS-REFERENCE TO RELATED APPLICATION

This application is based upon and claims the benefit of priority from the prior Japanese Patent Application No. 2014-233954, filed Nov. 18, 2014 the entire contents of them are incorporated herein by reference.

FIELD

An embodiment of the present invention relates to a sample processing apparatus and a sample processing method.

BACKGROUND

For example, in sample processing to inspect or analyze a sample such as blood or blood serum, a sample container is held and carried on a holder in an erect state, and various processes are conducted by various detectors arranged along a carrying path (Jpn Pat KOKAI Publication No. 2005-300357). In such sample processing, as a pre-process, sample containers are manually erected and inserted into a rack, and held and transferred one by one to the holder from the rack by a transfer device.

This requires a process of manually erecting a large number of sample containers and inserting the sample containers into the rack, and holding and transferring the sample containers one by one to the holder from the rack by the transfer device, which takes time and labor. Thus, improvement of processing efficiency is demanded.

DETAILED DESCRIPTION

First Embodiment

A sample processing apparatus 10 according to a first embodiment of the present invention will be hereinafter described with reference to FIG. 1 to FIG. 9. Components shown in each of the drawings are properly enlarged or reduced in size, or omitted. Arrows X, Y, and Z in the drawings indicate three directions perpendicular to one another, respectively. The arrow X extends along the carrying direction of a carrying unit 20, the arrow Y extends along the carrying direction of a holder carrying unit 60, and the arrow Z extends along the vertical direction.

Figure 1:
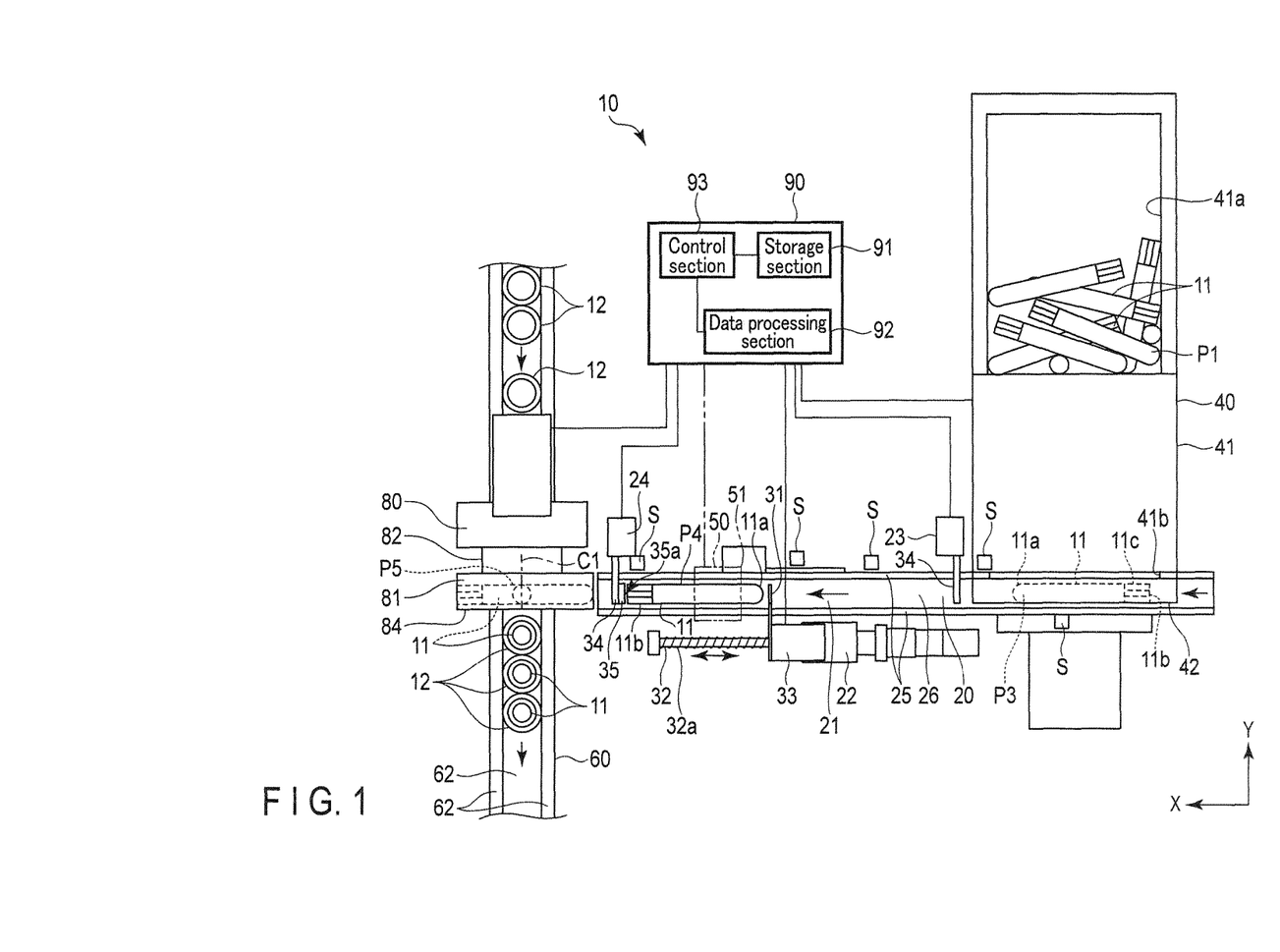
FIG. 1 is a plan view of a sample processing apparatus according to a first embodiment of the present invention.
Figure 2:
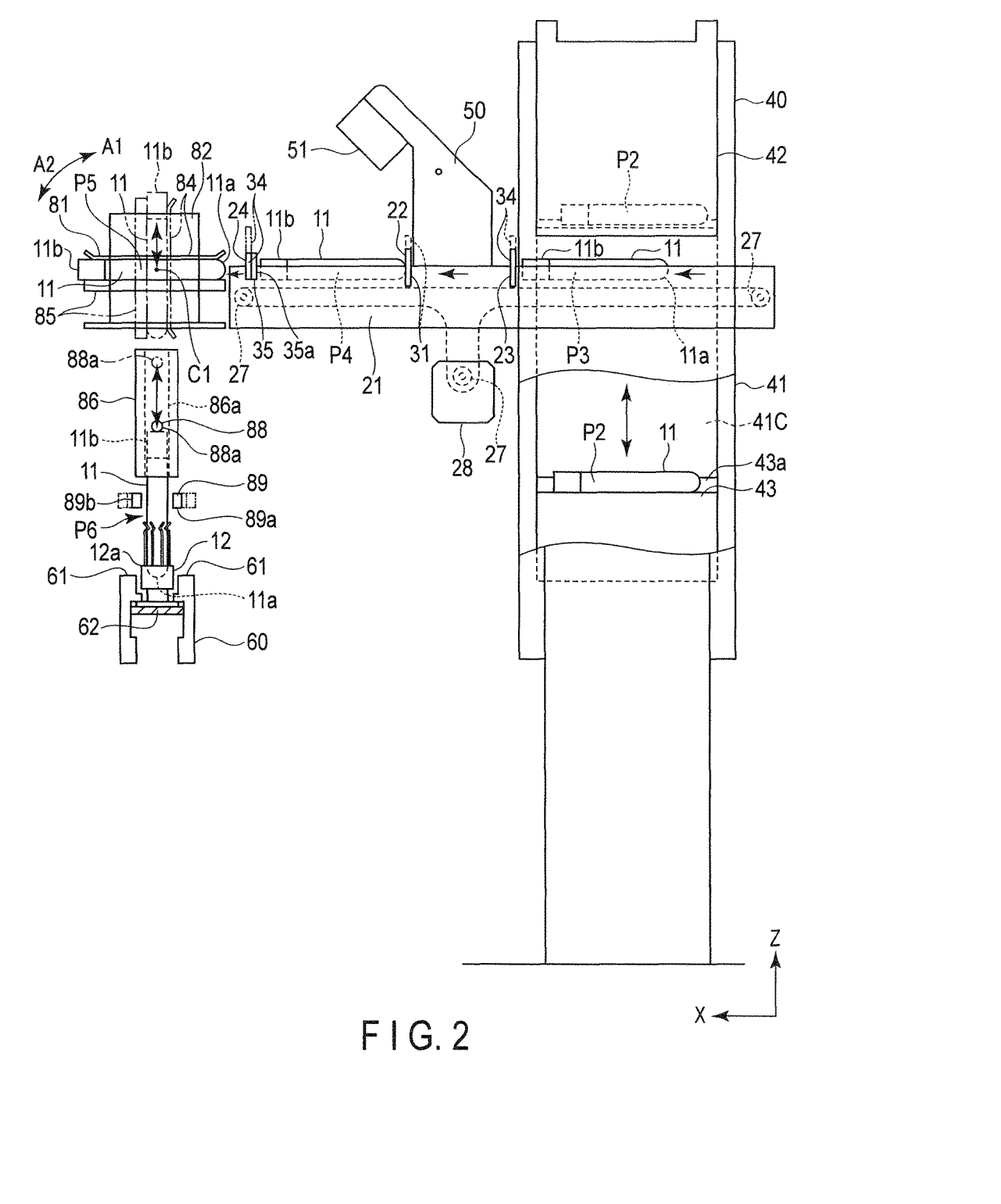
FIG. 2 is a front view of the sample processing apparatus according to the same embodiment.
Figure 3:
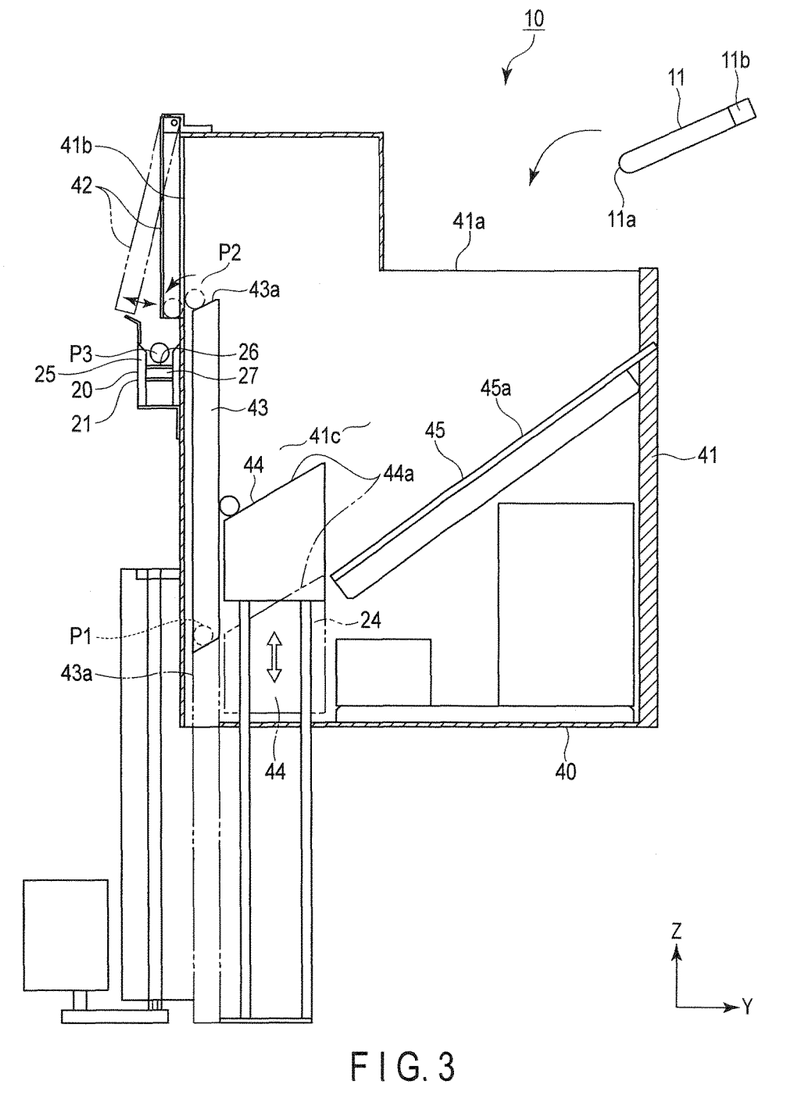
FIG. 3 is a side view of the sample processing apparatus according to the same embodiment.

FIG. 1 shows a top view showing the sample processing apparatus 10. FIG. 2 shows a front view of the sample processing apparatus 10. FIG. 3 is a partly sectional side view of a carry-in unit 40 of the sample processing apparatus 10.

The sample processing apparatus 10 is an apparatus which erects sample containers 11 and sets the sample containers 11 to a predetermined holder carrying path before various inspections, and is used as, for example, one of preprocessors of an analyzer.

The sample processing apparatus 10 comprises the carrying unit 20 which is a carrying section configured to be able to guide and carry the sample containers 11 mounted in a lying state to a predetermined route, the carry-in unit 40 which is a carry-in section to carry the sample containers 11 into a predetermined carrying path in the lying state, a detection unit 50 which is a detection section to detect the pose of the sample containers 11 in the lying state, the holder carrying unit 60 which carries a holder 12 holding the sample containers 11 along a predetermined path, a raising unit 80 which is a raising section to turn and raise the sample containers 11 and insert the sample containers 11 into the holder 12, laser sensors S which detect the presence of the sample containers 11 on the carrying path and which detects the arrival of the sample containers 11 at a predetermined position, and a controller 90 which controls the operation of each section.

The controller 90 is connected to the units 20, 40, 50, 60, 70, and 80, and the laser sensors S. The controller 90 comprises a storage section 91 to store various information, a data processing section 92 which performs data processing such as calculations and judging on the basis of identification information, and a control section 93 which controls the operation of each section.

The sample container 11 is a tubular sample container such as a test tube or a blood collection tube made of transparent glass or resin, and is formed into a closed-end circular cylindrical shape which has a bottom 11a and which is open at a top 11b and has a space to house a sample therein.

The sample processing apparatus 10 is configured to be able to process test tubes with plugs different in thickness and length. For example, several kinds of test tubes having a thickness of $\phi 13$ mm or $\phi 16$ mm and a length of 75 mm or 100 mm are targets.

In an opening at the top 11b of the sample container 11, a removable cap 11c which closes the opening is provided. The cap 11c comprises, for example, a hemogard plug or a rubber plug of various colors. A barcode including, for example, identification information is attached to the outer circumferential side surface of the sample container 11.

The carrying unit 20 comprises a belt-conveyer-type carrying mechanism section 21, a push-out mechanism section 22 configured to be able to push and move the sample container 11 in a predetermined direction, and stopper mechanism sections 23 and 24 which are provided at two places on the carrying path and which are configured to be able to regulate the movement of the sample container 11.

The carrying mechanism section 21 comprises a pair of guide rails 25 arranged with a given width along a predetermined carrying path, a carrying belt 26 made of, for example, rubber disposed over the carrying path between the guide rails 25, carrying rollers 27 provided in the rear of the carrying belt 26, and a motor 28 which serves as a drive source to rotationally drive the carrying rollers 27. The carrying path of the carrying mechanism section 21 is a path for the sample containers 11 which is formed on the carrying belt 26, and is set along the X-direction in the drawings. The carrying mechanism section 21 is configured to be able to carry the sample containers in the lying state along the predetermined carrying path including the lower part of a discharge opening 41b of the carry-in unit 40.

The sample containers 11 mounted on the carrying belt 26 between the pair of guide rails 25 are guided to and carried on the carrying path in the lying state in response to the conveyance of the carrying belt 26 attributed to the rotation of the carrying rollers 27.

Figure 4:
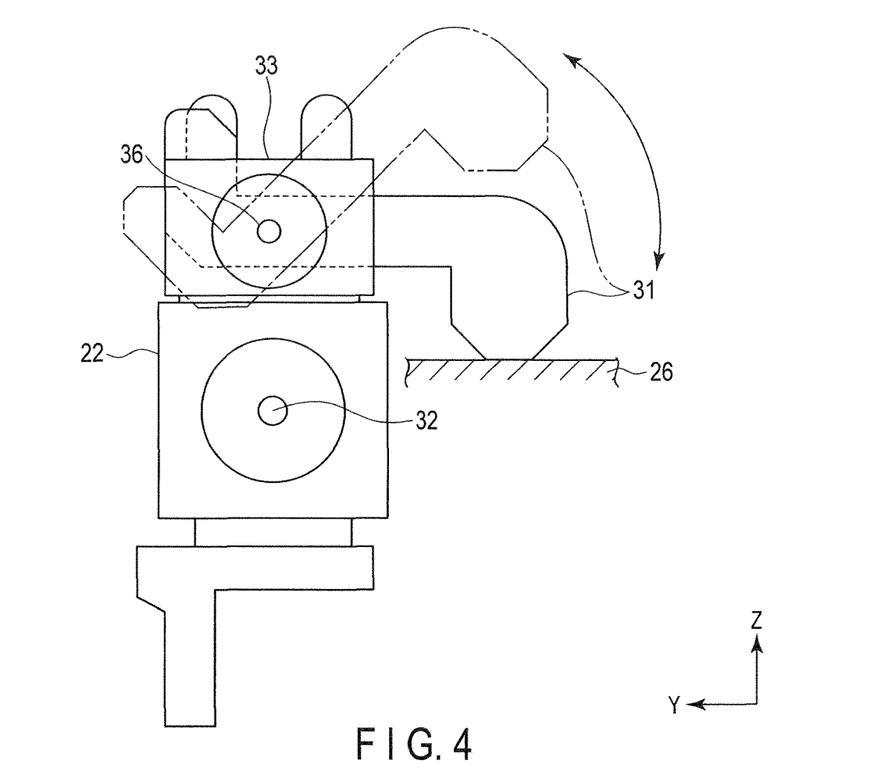
FIG. 4 is a side view of a push-out mechanism section of the same sample processing apparatus.

FIG. 4 is a side view showing the push-out mechanism section 22. The push-out mechanism section 22 shown in FIG. 4 comprises a blade 31 configured to be able to move into or evacuate from the carrying path by turning operation, a guide screw 32 which is provided beside the carrying path and which is configured to be rotatable, and a support portion 33 which engages with a spiral guide engagement protrusion 32a formed on the outer circumference of the guide screw 32 to support the blade 31.

The blade 31 is capable of turning operation by predetermined timing under the control of the control section 93, and is configured to be able to turn forward and backward around a predetermined shaft and thereby move back and forth between an entrance position to enter the carrying path to interfere with the sample container 11 and an evacuation position to deviate from the carrying path in order not to interfere with the sample container 11.

The guide screw 32 comprises a shaft extending along the carrying direction, and the guide engagement protrusion 32a which is spirally formed around the shaft. The guide screw 32 moves the support portion 33 back and fourth along the carrying direction in the forward and backward directions when the shaft repeatedly rotates forward and backward and stops by predetermined timing under the control of the control section 93.

The blade 31 which is engaged with and supported by the guide engagement protrusion 32a via the support portion 33 moves back and forth in the forward and backward directions of the carrying path in response to the rotational operation of the guide screw 32. The blade 31 that has entered the carrying path is guided by the guide screw 32 and moves forward in the carrying direction, so that the sample container 11 is pushed out and moved forward in the carrying direction even when the carrying belt 26 is stopped. The blade 31 that has evacuated is guided to the guide screw 32 and moved back in the carrying direction to the original position.

Figure 5:
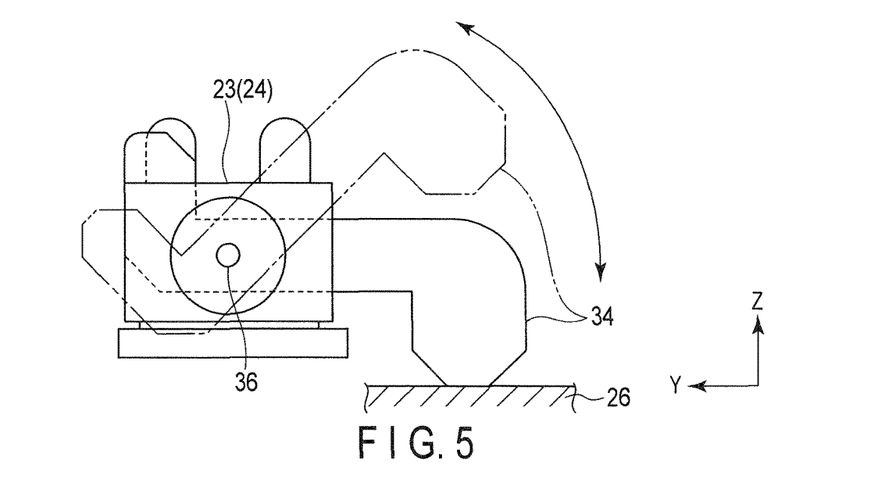
FIG. 5 is a side view of stopper mechanism sections of the same sample processing apparatus.

FIG. 5 is a side view of the stopper mechanism sections 23 and 24 seen from the back in the carrying direction. One stopper mechanism section 23 provided in the vicinity of the carry-in unit 40 comprises a blade 34 configured to be able to turn around a predetermined shaft 36. The blade 34 is configured to be able to enter the carrying path or evacuate from the carrying path by the turning operation. The blade 34 is provided at a position to be able to enter the carrying path.

The blade 34 is capable of rotational operation by predetermined timing under the control of the control section 93, and is configured to be able to turn forward and backward around a predetermined shaft 36 and thereby move back and forth between an entrance position to enter the carrying path to interfere with the sample container 11 and an evacuation position to deviate, for example, upward from the carrying path in order not to interfere with the sample container 11. When the blade 34 has entered the carrying path, the movement of the sample container 11 is regulated by the blade 34 and the sample container 11 stops even if the carrying belt 26 performs conveyance movement.

The other stopper mechanism section 24 provided at the end of the carrying direction comprises a blade 34 configured to be able to turn around a predetermined shaft 36 as shown in FIG. 5. The blade 34 is configured to be able to enter the carrying path or evacuate from the carrying path by the rotational operation. The blade 34 is provided at a position to be able to enter the carrying path.

As shown in FIG. 1, an abutment block 35 is provided in the rear of the blade 34 in the carrying direction. The abutment block 35 is, for example, a rectangular-parallelepiped block, and its end face on the rear side in the carrying direction forms an abutment surface 35a on which the sample container 11 abuts. The abutment surface 35a forms a plane that intersects at right angles with the carrying direction.

The blade 34 is capable of turning operation by predetermined timing under the control of the control section 93, and is configured to be able to turn forward and backward around a predetermined shaft 36 and thereby move back and forth between an entrance position to enter the carrying path to interfere with the sample container 11 and an evacuation position to deviate, for example, upward from the carrying path in order not to interfere with the sample container 11. When the blade 34 has entered the carrying path, the movement of the sample container 11 is regulated and stopped by the blade 34 even if the carrying belt 26 performs conveyance movement.

The carry-in unit 40 comprises a housing box 41 as a housing portion which forms a housing space 41c capable of housing the sample containers 11, an open-close door 42 provided at the discharge opening 41b formed in the side part of the housing box 41, a push-up blade 43 which ascends and descends in the housing box 41 to supply the sample containers 11 to the discharge opening 41b one by one, a drive source such as an air cylinder which causes the push-up blade 43 to ascend and descend, an auxiliary block 44 which ascends and descends in the vicinity of the push-up blade 43 to prompt the sample container 11 to move, and a drive source such as an air cylinder which causes the auxiliary block 44 to ascend and descend.

The housing box 41 is provided adjacent to the carrying path of the carrying section. The housing box 41 is a box having four sidewalls and a bottom wall, and forms a space to house the sample containers 11 therein. A supply opening 41a is formed in the upper surface of the housing box 41. A discharge opening 41b is formed in the upper part of the sidewall provided beside the carrying path. The open-close door 42 which opens and closes the discharge opening 41b is turnably provided on the upper edge of the discharge opening 41b. The lower edge of the discharge opening 41b is located slightly higher than the carrying belt 26. The carrying path of the carrying unit 20 is located immediately under the discharge opening 41b, and the carrying belt 26 is provided to correspond to the lower part of the lower edge of the open-close door 42.

A tilted blade 45 which forms a bottom surface tilted downward from the side of the supply opening 41a toward the side of the discharge opening 41b is provided in the internal space of the housing box 41. The sample containers 11 that have put in at random are collected to the side of the discharge opening 41b by the tilted blade 45.

The push-up blade 43 is provided adjacent to the inner side of the sidewall of the housing box 41 having the discharge opening 41b. The push-up blade 43 is configured to be able to ascend and descend in the upward and downward directions indicated by arrows in the drawings by the drive source. An upper end face 43a of the push-up blade 43 has a width that permits only one sample container 11 to be disposed, and is larger than, for example, the diameter of the sample container 11 and smaller than double the diameter. The upper end face 43a forms an inclined surface which is lower on the side of the discharge opening 41b. The sample containers 11 are pushed up one by one in response to the ascending and descending operation of the push-up blade 43, and supplied to the carrying path on the carrying belt 26 through the discharge opening 41b by the inclination of the upper end face 43a.

The auxiliary block 44 is provided adjacent to the rear side of the push-up blade 43. The push-up blade 43 is configured to be able to ascend and descend in the upward and downward directions indicated by arrows in the drawings by a drive source such as an air cylinder. An upper end face 44a of the auxiliary block 44 forms an inclined surface which continues to an upper surface 45a of the tilted blade 45 that has descended and which continues to the upper end face 43a of the push-up blade 43 that has descended. The inclination angle of the upper surface 45a of the tilted blade 45 is set to an angle equal to the inclination angle of the upper end face 44a of the auxiliary block 44 and or set to make an inclination slightly steeper than the upper end face 44a. The upper end face 44a of the auxiliary block 44 has an inclination slightly gentler than the upper end face 43a of the push-up blade 43. The auxiliary block 44 ascends and descends so that the sample containers 11 provided at random in various directions in the housing space 41c move to a small gap on the push-up blade 43 one by one in order. At the same time, the longitudinal directions of the sample containers 11 are aligned with X. The sample containers 11 are then individually sent to the discharge opening 41b one by one by the ascending of the push-up blade 43, and supplied onto the carrying belt 26 by the opening of the open-close door 42.

Figure 6:
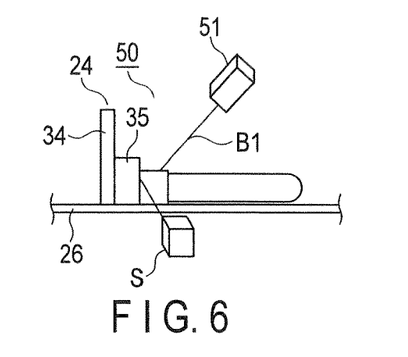
FIG. 6 is an explanatory diagram of a detection section of the same sample processing apparatus.
Figure 7A:
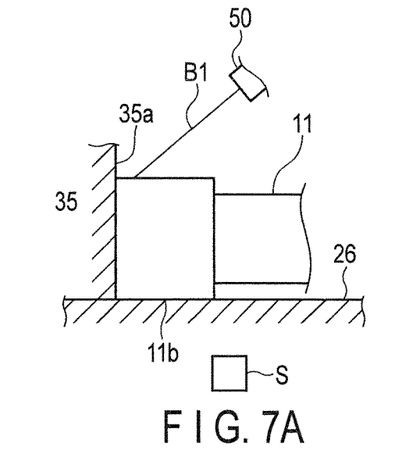
FIG. 7A is an explanatory diagram of a detection process according to the same embodiment.
Figure 7B:
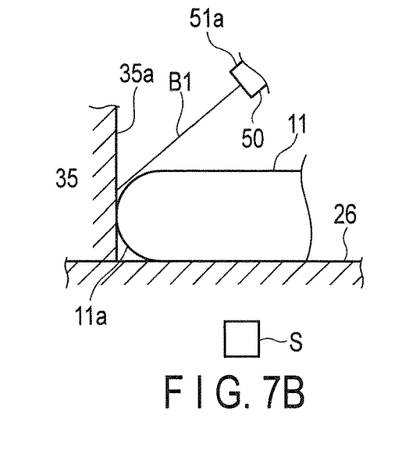
FIG. 7B is an explanatory diagram of the detection process according to the same embodiment.

FIG. 6, FIG. 7A, and FIG. 7B are explanatory diagrams of a detection process by the detection unit 50. FIG. 7A shows a situation in which the top 11b is located ahead in the carrying direction. FIG. 7B shows a situation in which the bottom 11a is located ahead. As shown in FIG. 6, FIG. 7A, and FIG. 7B, the detection unit 50 comprises a laser sensor 51 which detects the state of the sample container 11 in the lying state. The laser sensor 51 is a reflective displacement sensor, and is configured to be able to measure the distance to an object. Here, the shape difference between the cap 11c and the bottom 11a is used to determine the pose of the sample container 11 by the presence of a target part of the sample container 11 as pose information. The laser sensor 51 comprises a projection section which applies a laser beam B1 on an optical axis having a predetermined angle, and a light receiving section which receives the reflected laser beam B1. The laser sensor 51 applies the laser beam B1 at a predetermined angle and detects the reflected laser beam B1, and thereby detects the presence of a target part in the sample container 11 which has been carried to and stopped at a predetermined position in the lying state.

In the present embodiment, by way of example, the shape difference between the bottom 11a of the sample container 11 and the top 11b provided with the cap 11c is used so that the pose can be determined by the on/off state of the laser sensor. Here, the sample container 11 is formed so that the top 11b has a cornered cylindrical shape and so that the bottom 11a has a spherical shape with a curved corner. Therefore, as shown in FIG. 7, the laser beam B1 is projected toward the outer circumferential part of the end on the head side, and the pose of the sample container 11 is detected from the on/off state which indicates the presence of the laser beam reaching the light receiving section.

For example, as shown in FIG. 7A, when the top 11b provided with the cornered circular cylindrical cap 11c is located ahead, the laser sensor 51 turns on. Therefore, when the detection result in the laser sensor 51 is on, the control section 93 determines that the sample container 11 has such a pose that the top 11b is located ahead. In contrast, as shown in FIG. 7B, when the spherical bottom 11a with no corners is located ahead, the laser sensor 51 turns off. Therefore, when the detection result in the laser sensor 51 is off, the control section 93 determines that the sample container 11 has such a pose that the bottom 11a is located ahead.

That is, the control section 93 detects from the detection result in the laser sensor 51 which of the top 11b and the bottom 11a is located at the predetermined position that is on the head side, and can detect the pose of the sample container 11.

The holder carrying unit 60 is a conveyer-type carrying mechanism similar to the carrying unit 20, and a predetermined holder carrying path which passes an insertion point P6 located under a guide member 86 in the raising unit 80 is set in the holder carrying unit 60. The holder carrying path is a path for the holder 12 formed on a holder carrying belt 62, and is set along the Y-direction in the drawings. The holder carrying unit 60 comprises a pair of guide rails 61 disposed with a given width along the predetermined holder carrying path, the holder carrying belt 62 disposed between the pair of guide rails 61, a carrying roller which is rotationally driven in the rear of the carrying belt to move the carrying belt, and a motor or the like as a drive source to drive the carrying roller.

The holder 12 comprises a holding portion 12a having an insertion hole which is open in the upper part, holding pins 12b which are provided to stand upward from the upper end of the outer circumference of the holding portion 12a, and a holding ring 12c which holds the circumference of the holding pins 12b. Engagement grooves 12d which engage with the guide rails 25 are formed in the outer circumference of the holding portion 12a. The holder 12 which is empty is set on the carrying belt of the holder carrying unit 60 in advance, and the holder 12 is sent to the downstream side from the upstream side by the movement of the carrying belt. The holder 12 is stopped at the insertion point P6 along the holder carrying path by a holding mechanism 81, and the sample containers 11 are inserted into an insertion hole 12e of this holder one by one.

Figure 8:
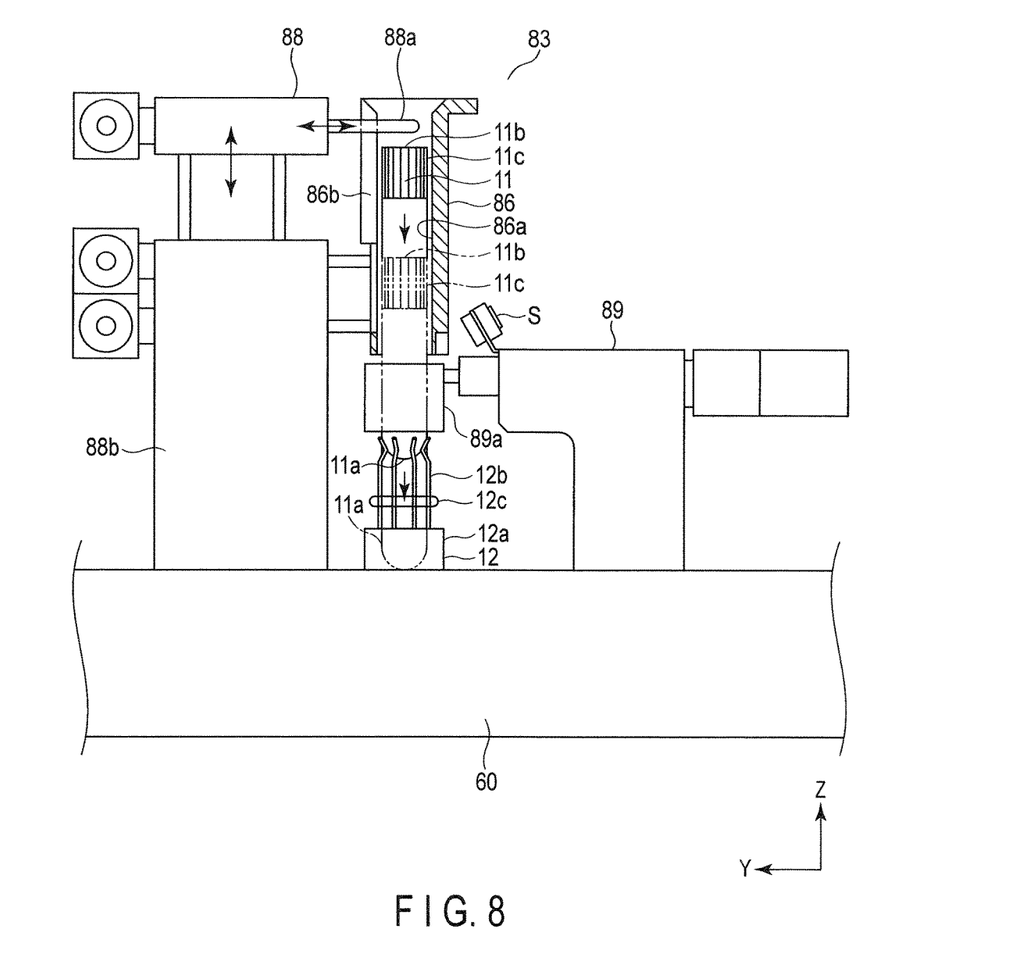
FIG. 8 is a side view of a raising unit according to the same embodiment.

The raising unit 80 comprises a holding mechanism section 81 configured to be able to hold the sample container 11 in the lying state in between and release the sample container 11, a turning mechanism section 82 which raises the sample container 11 by rotating the sample container 11 so that the top 11b is located on the lower side, and an insertion mechanism section 83 which inserts the erect sample container 11 into the holder 12.

The holding mechanism section 81 comprises a pair of holding blades 84 and 85 which are disposed to face each other and which are capable of holding the sample container 11 therebetween. The pair of holding blades 84 and 85 are configured to be able to open and close into and out of contact with each other in the Z-direction, for example, under the control of the control section 93. That is, the pair of holding blades 84 and 85 are configured to be able to be switched, for example, by the upward and downward movement of the upper holding blade 84 between a state to hold the sample container 11 in between with a small distance between the holding blades 84 and 85 and a state to release the sample container 11 with a great distance between the pair of holding blades 84 and 85.

The turning mechanism section 82 is configured to be able to turn the holding mechanism section 81 which holds the sample container 11 in both directions of arrows A1 and A2 around a predetermined turning axis C1. The turning operation of the turning mechanism section 82 is controlled by the control section 93. The direction of the turning is decided on the basis of information detected by the detection unit 50. That is, the turning mechanism section 82 turns 90 degrees in accordance with the detected direction the sample container 11, and a decision is thereby made on the direction of one of the arrows A1 and A2 so that the sample container 11 has such a pose that the bottom 11a of the sample container 11 is located on the lower side and the top 11b provided with the cap 11c is located on the upper side.

Figure 9:
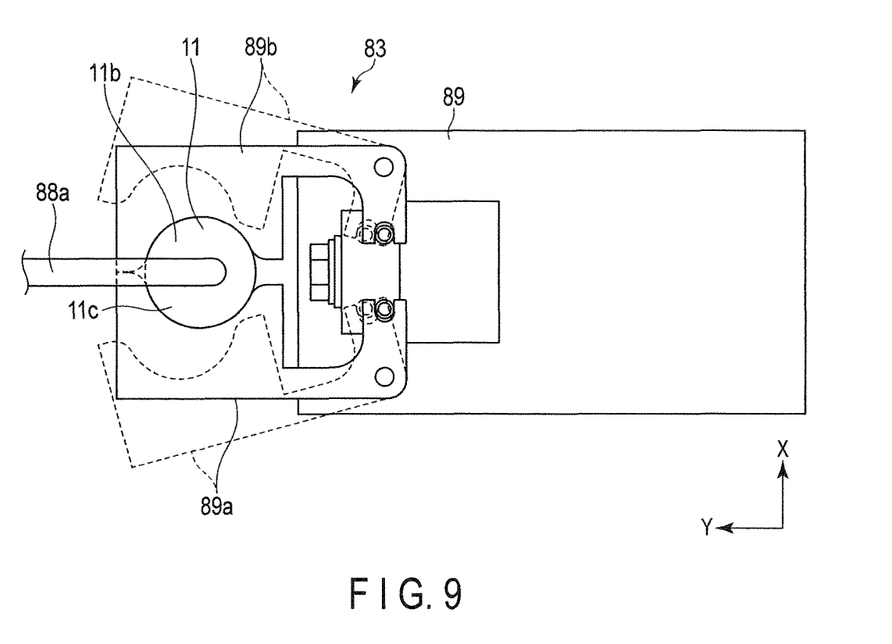
FIG. 9 is a plan view showing a part of the raising unit according to the same embodiment.

FIG. 8 is a partly sectional side view of the insertion mechanism section 83 of the raising unit 80. FIG. 9 is a top view of the insertion mechanism section 83. As shown in FIG. 8 and FIG. 9, the insertion mechanism section 83 comprises a guide mechanism section 87 which regulates the movement direction of the sample container 11 to the downward direction along the Z-direction, and a push-in mechanism section 88 which pushes in the sample container 11 downward. The guide mechanism section 87 comprises the cylindrical guide member 86 provided under the turning mechanism section 82, and a support portion 89 provided under the guide member 86. The guide member 86 has a circular cylindrical shape having a hole 86a extending in the Z-direction, and a slit 86b which is longitudinally cut out to permit the movement of a push-in shaft 88a is formed in a part of the circumferential wall of the guide member 86.

The support portion 89 comprises a pair of holing pieces 89a and 89b which open and close by turning, and is a chuck mechanism configured to be able to open and close by predetermined timing under the control of the control section 93. The support portion 89 supports the circumference of the sample container 11 which is pushed in downward by the push-in mechanism section 88, and regulates the movement direction to the upward and downward directions.

The push-in mechanism section 88 comprises a shaft 88a configured to be able to move back and forth, and a drive source 88b such as an air cylinder which causes the shaft 88a to ascend and descend. The shaft 88a is configured to be able to move between an entrance position to enter the carrying path of the sample container 11 supported by the guide mechanism section 87 and an evacuation position to evacuate from the carrying path. When the shaft 88a descends in the entering state, the cap 11c provided at the top 11b of the sample container 11 is pushed in downward, and inserted into the empty holder 12 set in the holder carrying unit 60 below.

Next, a sample processing method according to the present embodiment is described. The sample processing method according to the present embodiment comprises a carry-in process to carry the sample containers 11 into the carrying path one by one by the carry-in unit 40, a carrying process to sequentially send the sample containers 11 to each process position in the lying state one by one by the carrying unit 20, a detection process to detect the pose of the sample container 11 in the lying state by the detection unit 50, a raising process to hold the sample container 11 by the holding mechanism section 81 of the raising unit 80 and turn and raise the sample container 11 by the turning mechanism section 82, and an insertion process to insert the raised sample container 11 into the holder 12 underneath by the insertion mechanism section 83 of the raising unit 80. These processes are controlled by the control section 93, and a series of carry-in, carrying, detection, holding, turning, opening, and holder insertion processes are sequentially performed for one sample.

The sample containers 11 are housed in the housing space 41c of the housing box 41. The sample containers 11 are put in at random from the supply opening 41a by an operation, for example, after blood collection. At the same time, the sample containers 11 are collected to a collection position P1 at the lower end on the side of the discharge opening 41b by the tilted blade 45 in the housing space 41c.

As the carry-in and carrying processes, the control section 93 causes the push-up blade 43 and the auxiliary block 44 to ascend and descend at predetermined time intervals, and opens and closes the open-close door 42 at predetermined time intervals. As a result of the ascending of the push-up blade 43, the sample containers 11 collected at the bottom of the housing space 41c on the side of the discharge opening 41b ascend one by one, and are sent to an ascending position P2 in the rear of the open-close door 42. The sample containers 11 then fall down due to the opening of the open-close door 42, and are supplied to a supply position P3 on the carrying belt 26 provided under the discharge opening 41b.

The ascending and descending operations of the push-up blade 43 and the auxiliary block 44 prompt the sample containers 11 to move, and the sample containers 11 are sequentially sent one by one to the upper end face 43a of the push-up blade 43. By the repetition of this operation, the poses of the randomly housed sample containers 11 are aligned one by one in order at predetermined time intervals so that their longitudinal directions extend along the X-direction, and the sample containers 11 are automatically sent to the supply position P3. At this point, which of the top 11b and the bottom 11a is located ahead in the carrying direction is not decided, and varies according to the sample containers 11.

As the carrying process, the control section 93 repeats the conveyance movement and stopping of the carrying belt 26 at predetermined time intervals, and also moves the stopper mechanism section 24 and the blades 31 and 34 of the push-out mechanism section 22 back and forth and moves the blade 31 forward and backward. The sample container 11 located at the supply position P3 is sent forward by the evacuation of the blade 34 of the stopper mechanism section 24 and the conveyance movement of the carrying belt 26. When the sample container 11 reaches a detection position P4, the sample container 11 is brought into abutment with the abutment surface 35a of the abutment block 35 provided on the blade 34 by the second stopper mechanism section 24, and stops. In this stop state, the control section 93 controls the detection unit 50 to apply the laser beam B1 toward the outer circumferential part of the head side of the sample container 11 from the projection section of the laser sensor 51. From the on/off detection result which indicates the presence of the laser beam reaching the light receiving section, the pose of the sample container 11, that is, which of the top 11b and the bottom 11a is located ahead is determined (detected).

For example, as shown in FIG. 7A, when the top 11b provided with the cap 11c is located ahead, the laser sensor 51 turns on. Therefore, when the laser sensor 51 is on, it is determined that the sample container 11 has such a pose that the top 11b is located ahead.

In contrast, as shown in FIG. 7B, when the bottom 11a is located ahead, the laser sensor 51 turns off. Therefore, when the laser sensor 51 is off, it is determined that the sample container 11 has such a pose that the bottom 11a is located ahead.

On the basis of the detection result in the laser sensor 51, the control section 93 decides the rotation direction in the raising unit 80 so that the bottom 11a of the sample container 11 is lower.

By the timing of the end of the detection process, the second stopper mechanism section 24 is released to evacuate the blade 34, and the guide screw 32 is rotated while the blade 31 of the push-out mechanism section 22 is disposed at the entrance position, and then the sample container 11 is pushed out and sent to a holding position P5 ahead.

The control section 93 controls the holding mechanism section 81, and repeats holding and releasing the sample container 11 by given timing and turns the turning mechanism section 82 holding the sample container 11 90 degrees in a desired direction, thereby raising the sample container 11.

At the same time, the control section 93 controls the turning direction in accordance with the pose of the sample container 11 detected by the detection unit 50 so that that the bottom 11a is located on the lower side after the turning. For example, in the case of the pose such that the top 11b is located ahead in the carrying direction, the sample container 11 is rotated in a clockwise first rotation direction A1. In the case of the pose such that the bottom 11a is located ahead in the carrying direction, the sample container 11 is rotated in a counterclockwise second rotation direction A2.

The sample container 11 turns in the turning mechanism section 82 and is thereby erected, and falls down when the holding state is released by the holding mechanism section 81. The sample container 11 is guided to the guide hole 86a of the guide member 86 provided under the holding mechanism section 81 and then sent to the insertion position P6. The carrying belt of the holder carrying unit 60 is provided at the insertion position P6, and the empty holder 12 is set in advance.

The control section 93 controls the holder carrying unit 60 to repeat the conveyance operation and stopping of the holder carrying path by given timing. The control section 93 also controls the guide mechanism section 87 of the insertion mechanism section 83 to repeat holding or releasing the outer circumference of the sample container 11, and controls the push-in mechanism section 88 to perform the back-and-forth movement and ascending and descending operation of the shaft 88a. By this operation, the sample container 11 sent to the insertion position P6 in an erect state is guided downward and pushed in, and the sample containers 11 are sequentially inserted into the empty holder 12 sent from the upstream of the holder carrying path. Further, in response to the conveyance movement of the holder carrying unit 60, the holder 12 in which the sample containers 11 are inserted is sent to the downstream.

The following advantageous effects are obtained by the sample processing apparatus 10 and the sample processing method according to the present embodiment: The sample containers 11 that have been put in at random are sent one by one, the poses of the sample containers 11 are aligned, the sample containers 11 are erected so that the bottoms 11a are located on the lower side, and can be disposed in the holder 12. Therefore, the carry-in process of the sample containers 11 can be efficiently performed. Moreover, it is possible to omit the operation of manually raising and inserting the sample containers one by one, for example, on a rack.

It is also possible to easily detect, with simple equipment, the pose of the sample container 11 because the bottom 11a and the top 11b of the sample container 11 are distinguished from each other from the state of the laser applied to the predetermined position of the abutment surface 35a by the laser sensor 51.

The present invention is not completely limited to the embodiment described above, and modifications of components can be made in the embodiment without departing from the spirit thereof. Each of the components shown by way of example in the above embodiment may be eliminated, and the shape, structure, and material of each of the components may be changed. Further, various inventions can be made by properly combining the components disclosed in the embodiment described above.

What is claimed is:

1. A sample processing apparatus comprising:
   a sensor configured to detect pose information regarding a sample container which has a head portion and a bottom portion and is configured to house a sample;
   a carrying mechanism configured to carry the sample container in a lying state;
   a raising mechanism comprising:
      a holding mechanism which has a pair of holding blades disposed to face each other and to be separated from each other, the holding blades configured to hold in between and release the sample container in the lying state, the holding mechanism being rotatable in normal and reverse directions around a rotational axis that extends in a horizontal direction and is defined at a position between the head portion and the bottom portion of the sample container;
      a controller configured to determine a rotation direction of the holding mechanism as either normal or reverse direction, based on the pose information indicating an orientation of the sample container; and
      a turning mechanism which turns the holding mechanism in the rotation direction to turn and raise the sample container upright, and at the same time to position the sample container into a uniform orientation with respect to other sample containers, with the bottom portion being located at a lower level than the head portion such that the sample in the sample container contacts the bottom portion of the sample container; and
   an insertion mechanism comprising:
      a guide member provided under the holding mechanism, the guide member configured to support a circumference of the upright sample container that falls when the holding blades are released, and thereby to regulate the sample container to move vertically; and
      a shaft formed in a part of the wall of the guide member and configured to push the sample container down vertically,
      wherein the insertion mechanism inserts the upright sample container into a holder provided under the holding blades and having an insertion hole that opens in an upper part of the holder.

2. The sample processing apparatus according to claim 1, wherein the controller is configured to control the operation of the raising mechanism on the basis of the pose information, wherein the sample container is a test tube in which outer circumferential shapes of the top and bottom portions are different from each other, with a stopper provided in the head portion, the sensor comprises a laser sensor which detects, as the pose information, the outer circumferential shape of an end portion of the sample container at a predetermined position.

3. The sample processing apparatus according to claim 1, further comprising:

a carry-in mechanism, the carry-in mechanism comprising a housing portion in which a housing space configured to house more than one sample container and a discharge opening communicating the housing space to the outside are formed, and a push-up blade which is configured to ascend and descend in the housing space and which individually pushes up the sample containers and sends the sample containers to the discharge opening when the push-up blade has ascended;

a carrying mechanism configured to carry the sample containers in the lying state along a predetermined carrying path including the lower part of the discharge opening;

a holder carrying mechanism which is provided under the raising mechanism and which carries the holder configured to hold the sample containers in an erect state; and an insertion mechanism which pushes and inserts the sample containers in the erect state into the holder.

4. The sample processing apparatus according to claim 2, further comprising:

a carry-in mechanism, the carry-in mechanism comprising a housing portion in which a housing space configured to house more than one sample container and a discharge opening communicating the housing space to the outside are formed, and a push-up blade which is configured to ascend and descend in the housing space and which individually pushes up the sample containers and sends the sample containers to the discharge opening when the push-up blade has ascended;

a carrying mechanism configured to carry the sample containers in the lying state along a predetermined carrying path including the lower part of the discharge opening;

a holder carrying mechanism which is provided under the raising mechanism and which carries the holder configured to hold the sample containers in an erect state; and an insertion mechanism which pushes and inserts the sample containers in the erect state into the holder.

5. A sample processing method comprising:

carrying a sample container in a lying state along a predetermined carrying path, the sample container having a head portion and a bottom portion and being configured to house a sample;

detecting pose information indicating an orientation of the sample container by a sensor;

determining by a controller a rotation direction as either normal or reverse direction based on the pose information so that the sample container is raised upright with the bottom portion of the sample container being located lower than the head portion;

turning a turning mechanism configured to turn the sample container that is in the lying state, into the rotation direction around a rotational axis that extends in a horizontal direction and is defined by a position between the head portion and the bottom portion of the sample container so that the sample container is raised upright such that the sample in the sample container contacts the bottom portion of the sample container, wherein the turning mechanism comprises a holding mechanism which has a pair of holding blades disposed to face each other and to be separated from each other, the holding blades configured to hold in between and release the sample container in the lying state, and the holding mechanism is rotatable in normal and reverse directions around a rotational axis that extends in a horizontal direction and is defined at a position between the head portion and the bottom portion of the sample container; and inserting the sample container into a holder provided under the holding blades and having an insertion hole in an upper part of the holder, by releasing the holding blades, allowing the sample container in an upright state to fall into a guide member provided on the holding mechanism, the guide member to support the outer circumference of the upright sample container, and pushing the sample container down by a shaft configured to push the sample down into a holder.

6. The sample processing apparatus according to claim 1, wherein the holding mechanism is configured to hold an outer circumferential surface of the sample container carried in the lying state with either one of the head portion and the bottom portion in front in a carrying direction, and the holding mechanism is rotatable in normal and reverse directions, with a position between the head portion and bottom portion of the sample container serving as a rotational center.

* * * * *